Jan. 14, 1941. E. A. PEIRCE Plant Pat. 438
HYBRID TEA ROSE PLANT
Filed July 18, 1940
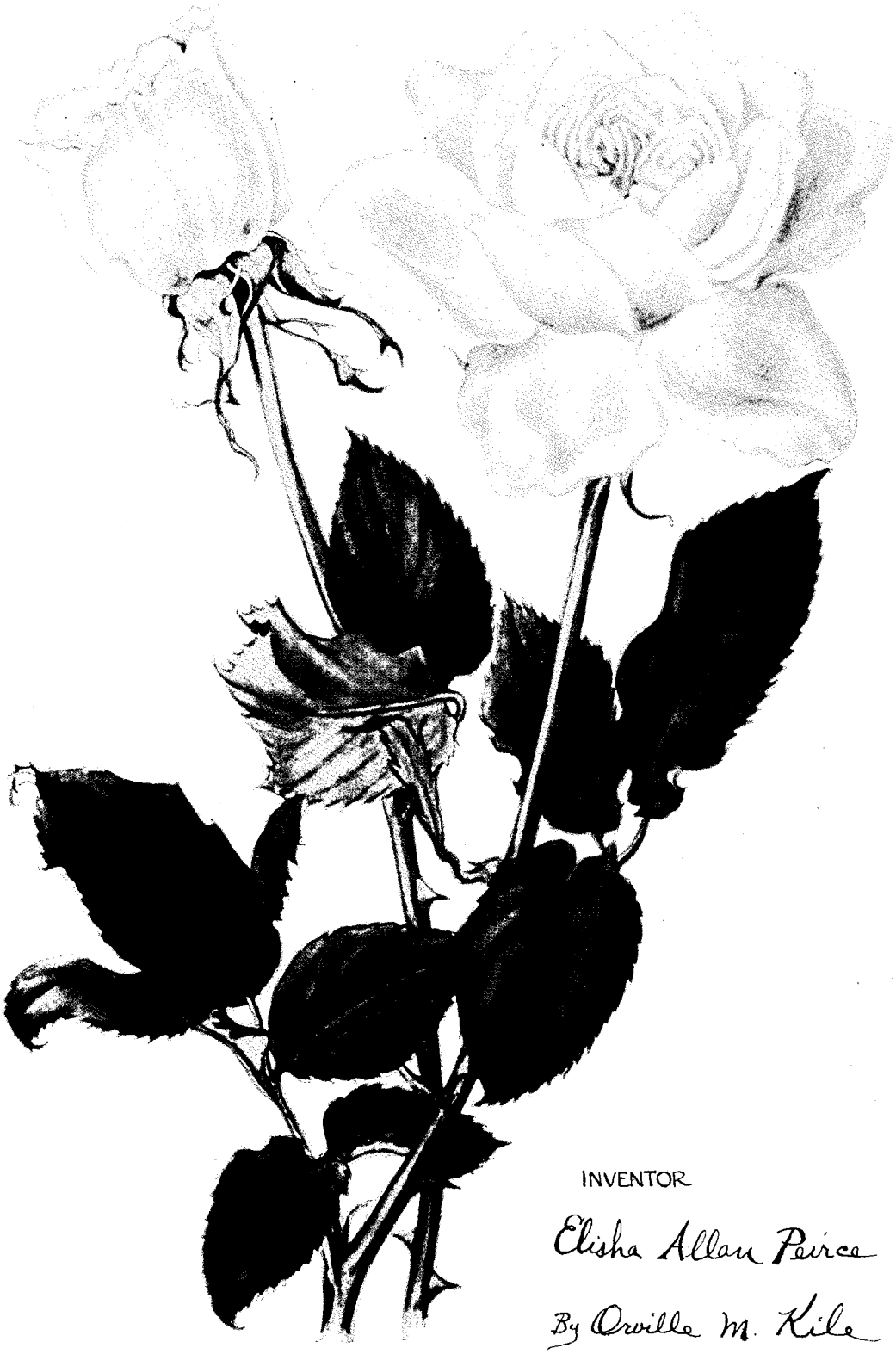
INVENTOR
Elisha Allan Peirce
By Orville M. Kile
PLANT PATENT AGENT Patented Jan. 14, 1941

Plant Pat. 438

UNITED STATES PATENT OFFICE

438

HYBRID TEA ROSE PLANT

Elisha Allan Peirce, Waltham, Mass., assignor to Peirce Brothers, Waltham, Mass.

Application July 18, 1940, Serial No. 346,201

1 Claim. (Cl. 47—61)

My present discovery relates to a new and distinct variety of everblooming hybrid tea rose plant which originated as a sport branch on a Talisman rose plant grown in the greenhouses of Peirce Brothers at Waltham, Massachusetts.

Many of the characteristics of the well-known Talisman are apparent in this new rose but several important new features are found. The principal differences between my new variety and its parent reside in the color, aroma, foliage and growth. The new variety has a very strong tea fragrance which persists throughout the life of the blossom. Its general color tone varies considerably between specimens and is difficult to match with any available color guide. However, the general color effect is of bright rose to strawberry pink with a suffusion of salmon-orange, the whole changing to deep pink after several days. The foliage of the new variety is not the usual Talisman type but is more like the Ophelia type foliage, being light green, close together, and high on the stem, and with a tendency to enfold the stem. Its growth is much stronger than that of its parent.

This new variety has been asexually reproduced by budding until a considerable quantity of stock has been accumulated, and its distinguishing characteristics have proved to be fixed.

The original illustration accompanying this application shows in approximately true colors, two specimens of this variety—one an opening bud indicating the characteristic Talisman form, and the other blossom almost entirely opened, indicating particularly the great number of central petals.

Following is a detailed description of this new variety, color designations being in accordance with Ridgway's Color Standards and Nomenclature, except where the dictionary term is obviously intended.

*The plant*

Growth: Vigorous, upright bush. Stronger growth than that of its parent.

Blooming habit: Continuous bloomer. Flowers borne singly on long stems.

Stems: Strong, stiff, Oil Green (Plate V).

*Nodes.*—Close together.

Thorns: Average number for roses. Sharp; downward-pointing; white with pinkish tinge.

*Prickles.*—None.

Foliage:

*Quantity.*—Abundant.

*Leaves.*—Compound with 3 to 7 leaflets, usually 5.

*Substance.*—Leathery; soft.

*Color.*—Upper surface between Forest Green (Plate XVII) and Dark Cress Green (Plate XXXI). Under surface approximately Light Elm Green (Plate XVII).

*Leaflets.*—Three to seven. *Shape*—oval with rounded base and acute to acuminate apex. *Size*—terminal leaflet is usually large compared to lateral leaflets. Terminal averages 3½ by 1¾ inches, while lateral averages 2½ by 1⅜ inches. *Margin*—sharply and singly serrated; undulating.

*Rachis.*—Smooth; slender; grooved on upper surface; same color as stems.

*Stipules.*—Long; narrow; clinging. Points very acute.

*Arrangement.*—Close together and high on stems, with tendency to enfold stems just above point of attachment.

*The flower*

Bud:

*Size.*—Large.

*Form.*—Ovoid. Opens into modified urn shape characteristic of Talisman.

*Calyx.*—Large, smooth.

*Sepals.*—Long; slightly foliaceous; turn backward very early. Outer surface is same color as peduncle, inner surface is covered with gray fuzz except on foliaceous tips.

*Peduncle.*—Strong; short; Oil Green (Plate V).

*Color.*—Each petal has a central streak of Maize Yellow (Plate IV) with a definite marking where the petals were first exposed to the sun. Base is Empire Yellow (Plate IV). The principal portion of the bud is nearer Begonia Rose (Plate I) than any other color shown in Ridgway's, but it is very much darker. It would fall somewhere in the range between Begonia Rose (Plate I) and Eugenia Red (Plate XIII).

Blossom:

*Borne.*—Singly and on long stems.

*Size.*—Large, 4 to 5 inches in diameter.

*Form.*—Characteristic Talisman form although much larger and fuller. Inner petals much smaller than outer ones and very much folded, imbricated, and often somewhat quartered in their arrangement. When the blossom is fully opened this arrangement displays a flat center of small petals surrounded by a frame of larger petals, with some of the pistils and stamens usually visible.

*Color.*—There is a great variation of color as between specimens and the color ranges from Strawberry Pink (Plate I) to the color described for the bud. The general color effect of a typical opening blossom is between Carrot Red (Plate XIV) and Light Coral Red (Plate XIII) in the central portion, with a frame of larger petals which are from Geranium Pink (Plate I) to approximately Spinel Pink (Plate XXVI). It then becomes Strawberry Pink (Plate I) to Carrot Red (Plate XIV) in the center, surrounded by larger petals slightly darker and with a suffusion of Spinel Pink (Plate XXVI). After about four days in a warm room, the typical flowers have become approximately Jasper Pink (Plate XIII). *Aiglet*—is Empire Yellow (Plate IV) on outside of petal and Light Cadmium (Plate IV) on the inner surface.

*Petalage.*—From 60 to 75 petals in the months of April and May in my greenhouses.

*Fragrance.*—Has unusually intense and enduring tea fragrance.

Petals:

*Shape.*—Outer petals are almost round, with a single point or flute at the top of each.

*Size.*—Outer petals are large, inner ones very small and short.

*Substance.*—Heavy.

*Color Distribution.*—Color is rather evenly distributed over individual petals, with the exception of the aiglet and the suffusion therefrom. Slightly darker on reverse side of petal and usually with a line of Maize Yellow (Plate IV) extending up the center.

Reproductive organs:

*Stamens.*—Many; surround pistils. *Filaments*—tinged with Carnelian Red (Plate XIV); uneven in length. *Anthers*—large; approximately Deep Chrome (Plate III).

*Pistils.*—Many; bunched. *Styles*—hairy; white, tinged with red at top. *Stigmas*—Maize Yellow (Plate IV).

*Calyx.*—Large; composed of five sepals.

*Sepals.*—Long, slightly foliaceous. Outer surface same color as peduncle; inner surface covered with gray fuzz.

Having thus disclosed my discovery, I claim:

A new and distinct variety of hybrid tea rose plant displaying many characteristics of the Talisman but characterized particularly by its strong growing habits, its light green foliage situated high on the stems; its strong, stiff stems with short internodes which serve to bring the foliage close together; and its large blossoms with numerous, imbricated petals, intense and enduring tea fragrance, and distinctive blended coloring of both bud and blossom substantially as described and shown.

ELISHA ALLAN PEIRCE.